United States Patent

Silvanov

[11] 4,067,335
[45] Jan. 10, 1978

[54] MATTER COLLECTING UNIT

[76] Inventor: Beverley Silvanov, 99 Gloucester Avenue, London NW1, England

[21] Appl. No.: 656,799

[22] Filed: Feb. 10, 1976

[30] Foreign Application Priority Data

Feb. 12, 1975 United Kingdom .................. 5988/75

[51] Int. Cl.² .............................................. A61F 5/44
[52] U.S. Cl. .................................................... 128/283
[58] Field of Search ............... 128/283, 294, 295, 2 F; 119/95; 4/121, 142

[56] References Cited

U.S. PATENT DOCUMENTS

| 3,577,989 | 5/1971 | Anderson | 128/283 |
| 3,619,822 | 11/1971 | Carmichael | 4/142 |
| 3,802,418 | 4/1974 | Clayton | 128/283 |
| 3,875,903 | 4/1975 | Sarvary | 119/95 |
| 3,878,572 | 6/1975 | Eriksson | 4/121 |
| 3,916,902 | 11/1975 | Lineberger | 128/295 |

Primary Examiner—Dalton L. Truluck
Assistant Examiner—Henry S. Layton

[57] ABSTRACT

Method and apparatus for collecting matter, particularly human waste matter. An annular member is fitted to a passage through which the material passes. A folded or rolled tube, closed at one end, is provided on the annular member, and collects the waste matter. The passage of the waste matter into the tube causes the tube to unfold or unroll. The portion of the tube containing the waste matter may then be sealed off and detached, leaving the remainder of the tube ready for collection of further matter.

18 Claims, 5 Drawing Figures

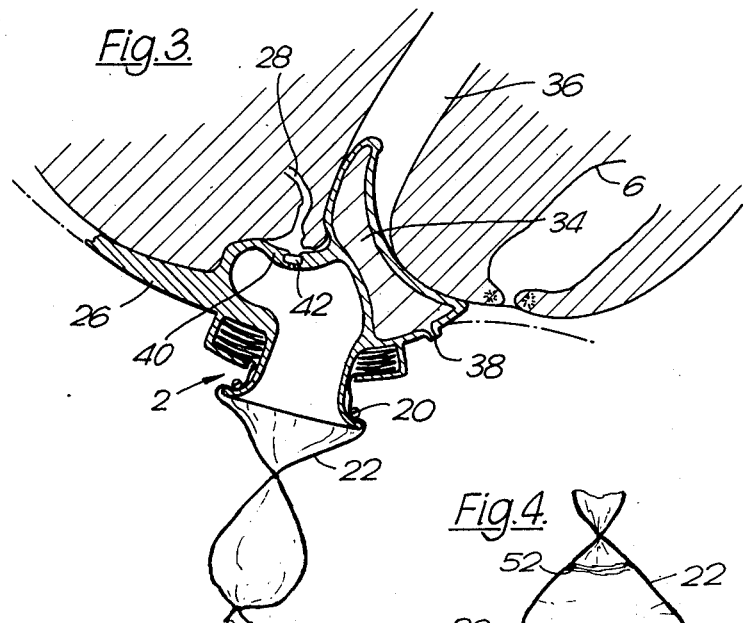
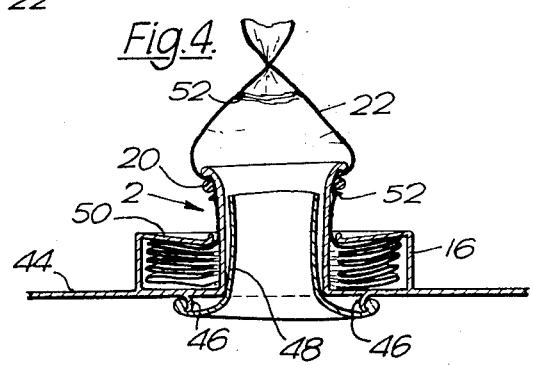
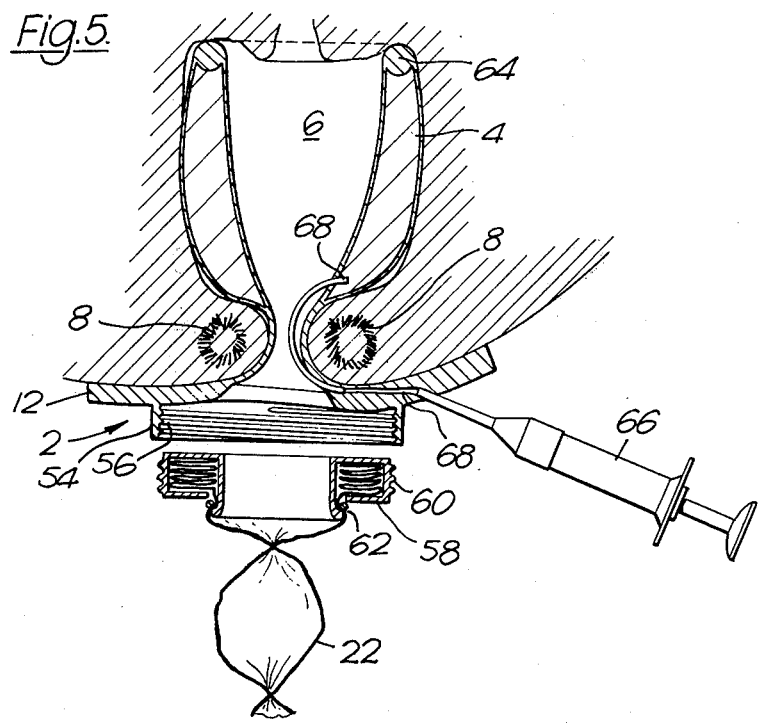

MATTER COLLECTING UNIT

This invention relates to a method and apparatus for collection of matter, either liquid, solid or gaseous.

A method of collecting matter in accordance with the invention comprises fitting one end of an annular member onto or into a passage through which the matter passes, a folded or rolled tube, closed at one end, being fitted into or onto the annular member, so that the matter, after passing through the annular member, is collected in the tube, which is forced to unroll or unfold, and sealing and detaching the part of the tube wherein the matter is retained, leaving the remainder of the tube in position to receive further matter.

Apparatus in accordance with the invention for collecting matter comprises an annular member, one end of which is adapted for connection to a passage through which the matter passes, and a folded or rolled tube, closed at one end, fitted to the member, the tube being normally retained, but being caused to unfold or unroll by passage of matter.

Though the invention may be employed in a wide variety of situations, it is particularly useful in the collection and disposal of human waste matter.

At present, the methods in use in hospitals for aiding bed-ridden patients when they wish to excrete or urinate suffer from many disadvantage. The process can be painful, particularly to those patients with serious ailments and who suffer pain when being moved. It can also be quite messy and unhygenic, and allow bedsheets and atmosphere to become contaminated or infected. The task is difficult also for nurses and the like, who have to lift the patients. The process can also be quite embarrassing for the patient.

The present invention overcomes these problems.

The annular member of apparatus in accordance with the invention may be formed so as to fit in the anal passage of the patient. For this purpose, the member may have a funnel comprising ribs connected by webs, the funnel being designed so that it will exert a light pressure on the walls of the anal passage. Alternatively, the funnel may be hollow and inflatable, so that it can be inserted into the anal passage in a collapsed condition and then inflated by passing a fluid (e.g. glycerine, or air) into its via a passage provided for this purpose. Faeces will then pass into the funnel, and through the annular member into the closed tube which is fitted around the end of the member, forcing the tube to unfold and so collect the excrement. When it is convenient the tube may be sealed by any of a variety of means, e.g. heat sealing, twisting, clamping etc. The tube is then cut and the part containing the waste matter disposed of.

Similar arrangements may be utilised for the collection of urine. Alternatively, the apparatus described may be adapted so that urine is led to an annular member provided for the collection of faeces, allowing the tube attached thereto to collect urine as well as faeces.

The apparatus of the invention may be incorporated into a garment.

It will be noted that the apparatus described above is not limited to use in hospitals, but may be designed so that people who suffer from incontinence may wear it at virtually all times. For males, for example, there may be provided a pair of trousers, on the inside of one leg of which is stitched a plastic lined pocket, in which the tube may enter after collecting urine and/or faeces. Similar devices may also be used for females. The tube may be sealed and detached when desired. This is far cleaner and more convenient than devices in use at the present.

As a preferred feature of the invention, the tube is located in a cassette, which is easily fitted onto the annular member, thus providing for easy replacement of tubes.

The invention will be further described by way of example, with reference to the accompanying drawings, in which:

FIG. 3 shows a further embodiment, designed to collect urine only from females.

FIG. 4 shows an embodiment for collection of urine from males.

FIG. 5 shows an alternative embodiment to that of FIG. 1.

Figure 1:
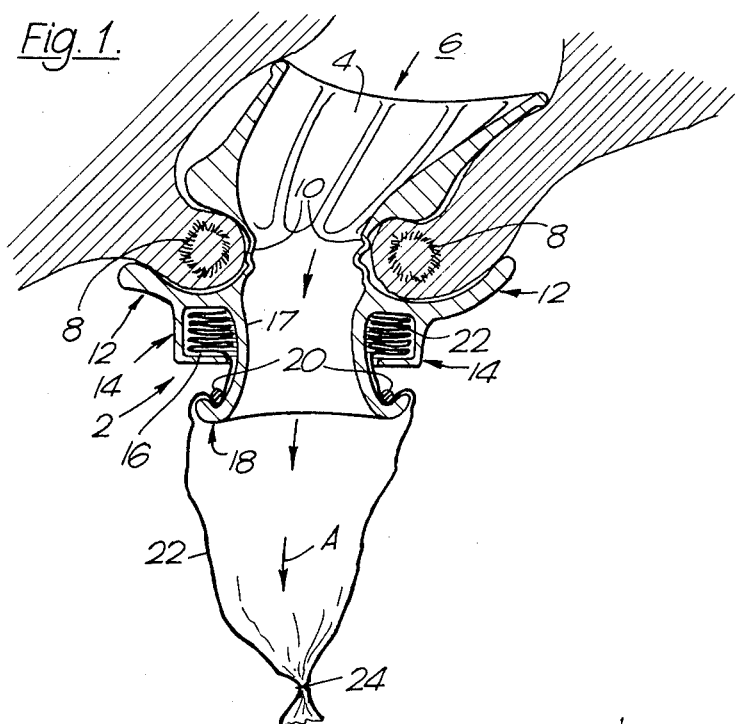
FIG. 1 shows an embodiment of the invention designed to collect faeces.

Referring to FIG. 1 an annular member is indicated generally by the numeral 2. At one end is formed connection means in the form of a funnel 4, consisting of ribs joined by webs, which is inserted in an anal passage 6. The funnel exerts a gentle pressure on the walls of the anal passage. At the exit of anal passage 6 are sphincter muscles 8. Here the funnel 4 is linked to the rest of the annular member 2 by a thin annular membrane 10. The membrane is so designed that it does not inhibit the movement caused by sphincter muscles 8.

On the member 2 is provided an annular flange 12, shaped to fit comfortably around the entrance of the anal passage 6.

An annular wall 14 is formed on the flange 12, providing a chamber 16 between wall 14 and the tubular portion 17 of the annular member 2.

The end 18 of annular member 2 is in the form of a lip, which holds a retaining ring 20 on the member 2.

A tube 22, folded concertina fashion to fit in the chamber 16, passes out of the chamber, between retaining ring 20 and the annular member 2, and around the lip at the end 18. The tube is sealed as indicated at 24.

Faeces passes down the anal passage 6, as indicated by the arrows A, through the annular member 2, and into the tube 22. The retaining ring 20 is designed so that it frictionally retains the tube 22, with just sufficient force so that the tube is forced to extend by the pressure of the faeces as it collects in the tube.

A patient using the device described above may have a specially designed bed or wheelchair, so that the tube 22 passes through a hole in the bed or wheelchair to a receptacle underneath. When it is convenient the tube may be sealed, and, if desired, detached and disposed of.

Sealing and detachment may be effected by a pair of heat-sealing scissors comprising two heating elements, one on each side of a standard pair of cutting elements. Thus the tube is automatically sealed at both sides of the cut when the tube is detached. Alternatively, the inside of the tube may be provided with spaced areas coated with pressure-sensitive adhesive, so that the tube may be sealed simply by squeezing the sides together. The tube may be scored in these areas so that portions may be easily detached.

Figure 2:
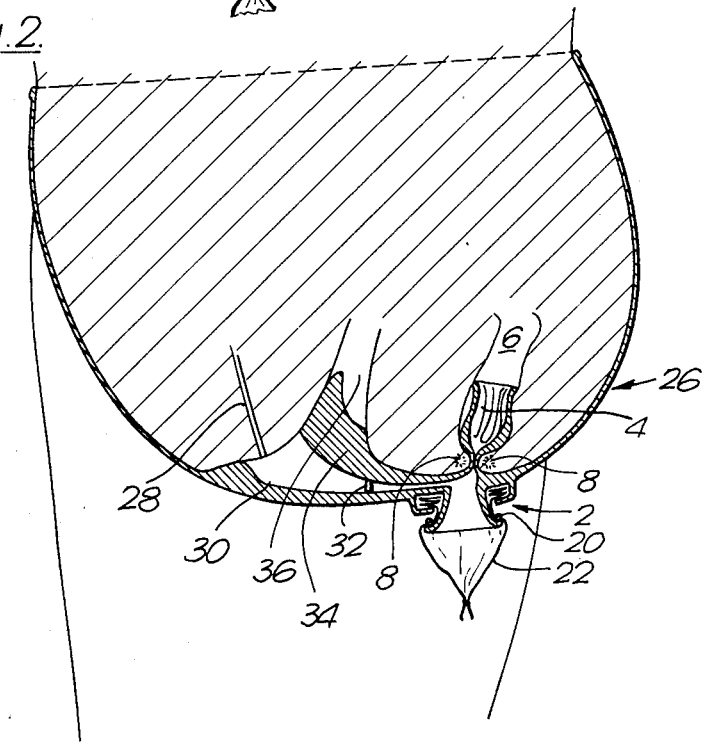
FIG. 2 shows another embodiment of the invention for use with females, designed to collect both urine and faeces.

FIG. 2 shows another embodiment of the invention, incorporated into a garment and designed to collect urine and faeces from a female. Some of the apparatus is similar to that shown in FIG. 1, and like parts given like reference numerals.

The annular member 2 is fitted into connection means in the form of a garment 26. The garment is preferably made of elasticated cotton or the like, with rubber or plastics material welded or welted to appropriate areas, where waste matter may come into contact with the garment, and designed so that urine from urine passage 28 is caused to flow along a channel 30 in the garment 26, into the annular member 2, through which it falls into tube 22. A small valve 32 may be formed over the channel so that no backflow will occur no matter what position the patient is in. An extension 34 may be formed in the garment 26 to fit over the entrance of the vagina 36, to ensure that no waste matter enters.

The apparatus is used in a similar way as the embodiment shown in FIG. 1.

FIG. 3 shows a similar arrangement, but used only for collecting urine from females. The extension 34 is formed of plastics material, and is hollow so that it may be inflated to a comfortable size by injecting for example glycerine from a syringe via passage 38 into the extension 34. A suitable valve (not shown) is incorporated into the passage so that the extension is kept inflated when the syringe is removed. A member 40 extends over the opening of the urine passage 28 and is provided with a heart-type valve 42 to prevent backflow.

FIG. 4 shows apparatus designed to collect urine from males, in which the annular member 2 is adapted to fit over a penis. The garment 44 is provided with an annular rim 46 over which connection means in the form of an open-ended sheath 48 is fitted. The sheath 48 fits closely around the penis, thus preventing backflow and consequent chafing.

The chamber 16 is provided with a sloping wall 50 which acts to further restrain the tube 22 so as to ensure that the tube does not extend unduly due to movement of the user causing the tube to work free. For similar purposes, the tube is provided with thickened or pleated annular portions 52 at spaced intervals, so that it is dispensed in segments as the portions 52 are restricted by retaining ring 20.

FIG. 5 shows an alternative embodiment to the apparatus of FIG. 1. In this case, the annular member 2 is provided with a rim 54 which has means for attachment 56 (e.g. a screw thread, a projection or recess, etc.) to a cassette 58, which has cooperating means for attachment 60.

The tube 22 is located in the cassette 58, and leads out of the cassette via an annular, restricting outlet 62. It will be appreciated that the tube may be easily replaced, simply by detaching cassette 58 from rim 54 and fitting a new cassette.

The funnel 4 is forced of hollow plastics material having a thickened 64 end and may be inflated to form a good fit on axial passage 6 by injecting fluid, by means of syringe 66, into passage 68 which is provided with a suitable valve (not shown) to prevent deflation when the syringe is removed. The funnel 4 may be provided with means (not shown) such as narrower annular portions, to ensure that it flexes suitably so that it does not restrict movements causing changes of shape of the anal passage.

It will be noted that use of the apparatus in hospitals is particularly advantageous, since it allows measurements and anaylses of patients' waste matter to be carried out cleanly and efficiently. However, the use of the apparatus of the invention for collecting human waste matter is also advantageous in many other situations, for example in space travel, etc.

The invention extends also to many other areas. It may be used for trapping any kind of animal excrement. It may be used for trapping animal sperm for experimentation or artificial insemination purposes.

I claim:

1. Apparatus for collecting human waste matter, said apparatus being wearable by a user, said apparatus comprising
   a tubular member, connection means for attaching the inlet end of said tubular member to a human waste passage to receive waste therefrom,
   a flexible tube having a closed end for receiving and retaining human waste matter passed through the outlet end of said tubular member, said flexible tube being contracted in its longitudinal direction in a storage attitude until use thereof is required, said flexible tube being comprised of successive waste matter receiving portions each of which can be severed in turn from the remainder of said flexible tube after use thereof, and said flexible tube being reclosed for delivery of matter into a succeeding portion after use of a preceding portion, and
   retainer means engageable with said flexible tube, said retainer means cooperating with said flexible tube to permit stepwise extension of said flexible tube out of said storage attitude into a waste receiving attitude to provide said successive waste matter receiving portions.

2. Apparatus as claimed in claim 1 wherein said contracted tube surrounds said tubular member.

3. Apparatus as claimed in claim 1, said retainer means comprising
   a friction ring surrounding said tubular member, said friction ring being disposed between that portion of said flexible tube in the storage attitude and the closed end of said flexible tube.

4. Apparatus as claimed in claim 1 including
   a storage chamber formed exteriorly of and coaxial with said tubular member, that portion of said flexible tube in the storage attitude being retained within said storage chamber.

5. Apparatus as claimed in claim 4 including
   a cassette connectable to said tubular member, said cassette defining said storage chamber.

6. Apparatus as claimed in claim 1, said connection means including
   a funnel connected to said tubular member, said funnel being structural for insertion into a human anal passage.

7. Apparatus as claimed in claim 6 wherein said funnel is of a hollow and inflatable structure, said structure including a passage provided for fluid to be passed thereinto for inflating said funnel as desired.

8. Apparatus as claimed in claim 1, said connection means including a tubular sheath structured to fit over a human penis.

9. Apparatus as claimed in claim 1 said connection means including
   an undergarment adapted to be worn by a human, said tubular member being fixed to said undergarment.

10. Apparatus for collecting human waste matter, said apparatus being wearable by a user, said apparatus comprising a tubular member, connection means for attaching the inlet end of said tubular member to a human waste passage, and a tube at least partially surrounding said tubular member, said tube having a closed end which closes off to atmosphere the outlet end of said tubular member, that part of said tube which surrounds, said tubular member being contracted in its longitudinal direction so that said tube may be progressively extended in a direction away from said tubular member to receive waste matter passed through said tubular member.

11. Apparatus as claimed in claim 10 including retainer means engageable with said tube, said retainer means serving to retain said tube against extension except as required to receive waste matter.

12. Apparatus as claimed in claim 11, said retainer means comprising a friction ring surrounding said tubular member, said friction ring being disposed between that portion of said tube in the contact attitude and the closed end of said tube.

13. Apparatus as claimed in claim 10 including a storage chamber formed exteriorly of and coaxial with said tubular member, the contracted portion of said tube being retained within said storage chamber.

14. Apparatus as claimed in claim 13 including a cassette connectable to said tubular member, said cassette defining said storage member.

15. Apparatus as claimed in claim 10, said connection means including a funnel connected to said tubular member, said funnel being adapted for insertion into a human anal passage.

16. Apparatus as claimed in claim 10, said connection means including a tubular sheath structured to fit over a human penis.

17. Apparatus as claimed in claim 10, said connection means including an undergarment adapted to be worn by a human, said tubular member being fixed to said undergarment.

18. A method of collecting human waste matter comprising the steps of attaching one end of a tubular member to a human waste passage by connection means in a manner that permits wearing of said tubular member by a user, said tubular member being provided with a flexible tube having a closed end for receiving and retaining human waste matter passed through said tubular member, contracting said flexible tube in its longitudinal direction into a storage attitude, thereafter extending said flexible tube in a direction away from the tubular member to provide a waste matter receiving portion for receiving waste matter passed through said tubular member, and detaching said waste matter receiving portion of said tube after waste matter has been received, the remaining portion of said tube having its end reclosed and left in position to receive further waste matter.

* * * * *

UNITED STATES PATENT AND TRADEMARK OFFICE
CERTIFICATE OF CORRECTION

PATENT NO. : 4,067,335
DATED : Jan. 10, 1978
INVENTOR(S) : Beverly Silvanov

It is certified that error appears in the above-identified patent and that said Letters Patent are hereby corrected as shown below:

Column 1, line 28, "disavantage" should be -- disadvantages --

Colum 1, line 46, "its" should be -- it --

Column 3, line 56 after "thickened" delete "64" and after "end" add -- 64 --

Column 5, line 25, "contact" should be -- contracted --

Signed and Sealed this

Eighth Day of August 1978

[SEAL]

Attest:

RUTH C. MASON
Attesting Officer

DONALD W. BANNER
Commissioner of Patents and Trademarks